(12) United States Patent
Milbourn

(10) Patent No.: US 7,472,495 B2
(45) Date of Patent: Jan. 6, 2009

(54) POSTURAL CORRECTIVE ANKLE STABILIZING INSOLE

(76) Inventor: Jack Milbourn, 2109 N. 8th St., Springfield, IL (US) 62702

( * ) Notice: Subject to any disclaimer, the term of this patent is extended or adjusted under 35 U.S.C. 154(b) by 306 days.

(21) Appl. No.: 11/349,599

(22) Filed: Feb. 8, 2006

(65) Prior Publication Data

US 2007/0180738 A1 Aug. 9, 2007

(51) Int. Cl.
*A43B 23/28* (2006.01)
(52) U.S. Cl. ............... 36/58.5; 36/43; 36/140
(58) Field of Classification Search ............ 36/80, 36/92, 58.5, 43, 140
See application file for complete search history.

(56) References Cited

U.S. PATENT DOCUMENTS

| | | | | |
|---|---|---|---|---|
| 747,390 | A * | 12/1903 | Echols | 36/58.5 |
| 884,520 | A * | 4/1908 | McIntire | 36/58.5 |
| 1,163,395 | A | 12/1915 | Cushman | |
| 1,409,060 | A * | 3/1922 | Mullinix | 36/58.5 |
| 1,832,736 | A * | 11/1931 | Raposy | 36/58.5 |
| 1,849,458 | A | 3/1932 | Jung | |
| 1,972,899 | A * | 9/1934 | Odell | 36/140 |
| 2,034,463 | A | 3/1936 | Dvlinsky | |
| 2,062,557 | A | 12/1936 | Clark | |
| 2,097,476 | A | 11/1937 | Silver | |
| 2,154,997 | A | 4/1939 | Schipper | |
| 2,194,637 | A | 3/1940 | Burger | |
| 2,522,681 | A * | 9/1950 | Leonard | 36/58.5 |
| 2,598,297 | A | 5/1952 | Pierson | |
| 3,320,347 | A | 5/1967 | Greenawalt | |
| 3,470,880 | A | 10/1969 | Pagliano | |
| 3,613,274 | A * | 10/1971 | Willey | 36/68 |
| 4,020,570 | A | 5/1977 | Shames | |
| 4,194,249 | A | 3/1980 | Thorneburg | |
| 4,314,411 | A | 2/1982 | Hanson | |
| 4,435,910 | A | 3/1984 | Marc | |
| 4,575,954 | A | 3/1986 | Bye | |
| 4,597,196 | A | 7/1986 | Brown | |
| 4,603,493 | A | 8/1986 | Eston | |
| 4,716,662 | A | 1/1988 | Bar | |
| 4,805,319 | A | 2/1989 | Tonkel | |
| 4,831,750 | A | 5/1989 | Muller | |
| 4,843,741 | A | 7/1989 | Yung-Mao | |
| 4,852,273 | A | 8/1989 | Hamy | |
| 4,879,821 | A * | 11/1989 | Graham et al. | 36/44 |
| 4,893,418 | A | 1/1990 | Ogden | |
| 4,897,938 | A | 2/1990 | Otsuka | |
| 4,906,425 | A | 3/1990 | Poussou | |
| 4,908,961 | A | 3/1990 | Purslow et al. | |

(Continued)

FOREIGN PATENT DOCUMENTS

DE 7230764 12/1972

(Continued)

*Primary Examiner*—Marie Patterson
(74) *Attorney, Agent, or Firm*—Law Office of Robert M. Patino

(57) ABSTRACT

An orthotic insole usable in an article for footwear for aligning a foot with its lower leg to provide balance and support having a support base, an expandable rail section moveable between a receiving position and a grabbed position around an outer edge of the foot, and an expandable rail section moveable from the receiving position to the grabbed position when the foot is placed in the article of footwear.

18 Claims, 3 Drawing Sheets

U.S. PATENT DOCUMENTS

| | | | |
|---|---|---|---|
| 4,955,148 A | 9/1990 | Padilla | |
| 5,003,708 A | 4/1991 | Daley | |
| 5,014,448 A | 5/1991 | Perrone | |
| 5,018,233 A | 5/1991 | Waterfield et al. | |
| 5,131,173 A | 7/1992 | Anderie | |
| 5,163,237 A | 11/1992 | Rosen | |
| 5,184,409 A | 2/1993 | Brown | |
| 5,203,096 A | 4/1993 | Rosen | |
| 5,228,164 A | 7/1993 | Graf et al. | |
| 5,231,723 A | 8/1993 | White et al. | |
| 5,233,767 A | 8/1993 | Kramer | |
| 5,266,062 A | 11/1993 | Runckel | |
| 5,335,517 A | 8/1994 | Throneburg et al. | |
| 5,724,753 A | 3/1998 | Throneburg et al. | |
| 5,729,918 A | 3/1998 | Smets | |
| 6,131,311 A | 10/2000 | Brown et al. | |
| 6,233,846 B1 * | 5/2001 | Sordi | 36/28 |
| 6,401,256 B1 | 6/2002 | Shreve | |
| 6,401,366 B2 | 6/2002 | Foxen et al. | |
| 6,446,267 B1 | 9/2002 | Shah | |
| 2002/0162250 A1 * | 11/2002 | Campbell et al. | 36/166 |
| 2004/0103561 A1 * | 6/2004 | Campbell et al. | 36/88 |
| 2004/0118020 A1 | 6/2004 | Hlavac | |
| 2004/0194348 A1 * | 10/2004 | Campbell et al. | 36/93 |
| 2005/0011086 A1 | 1/2005 | Goetze | |
| 2005/0081404 A1 * | 4/2005 | Hurd et al. | 36/58.6 |
| 2005/0188562 A1 | 9/2005 | Clarke et al. | |
| 2006/0021252 A1 | 2/2006 | Throneberg et al. | |

FOREIGN PATENT DOCUMENTS

| | | |
|---|---|---|
| JP | 49-109751 | 10/1974 |
| JP | 50-120631 | 9/1975 |
| JP | 52-2647 | 1/1977 |
| JP | 55-70804 | 5/1980 |
| JP | 63-125201 | 5/1988 |

* cited by examiner

POSTURAL CORRECTIVE ANKLE STABILIZING INSOLE

BACKGROUND OF THE INVENTION

The present invention relates to an orthotic insole usable in an article for footwear, and more particularly to such an orthotic insole used in shoes for aligning a foot with its lower leg to provide balance and support.

Insoles have generally been provided for shoes and other articles for footwear to reduce the shock force created when impact between the heel of the human body and a ground surface result in a reaction force when walking, running or doing like activities. Furthermore, insoles have been provided to add comfort and support when the body stands motionless by containing a variety of flexible or inflexible materials capable of being contoured to the shape of the underside of an individual's foot. Many insoles can be shortened by its length or width to be placed into an article for footwear according to the desired specifications of a user. Transferable insoles are preferred so that costs are minimized by negating the need to buy multiple insoles for each pair of shoes or articles for footwear a user might have.

However, current insoles lack a functional means of providing the above mentioned benefits and provide the ability to assist in correcting a musculoskeletal imbalance that occurs as people get older or injuries occur in various parts of the body. Bones in the arch of the foot are held in alignment by the plantar fascia tendons. Although these tendons are very strong, over time and/or stress, the plantar fascia tendons in the feet loose their elasticity in allowing the bones of the longitudinal arch of the foot to settle. When this condition takes place, the longitudinal arch begins to collapse forcing the entire foot and leg to rotate inward. This condition creates a body weight shift from the heel and the bones on the outside of the foot forward to the metatarsal bones (ball of the foot). The result is an unstable foundation and malalignment of the bones in the feet, ankles, knees and back. An unstable ankle joint is created, further stretching the tendons and producing greater instability. The unstable condition often is responsible for many ankle injuries and accidental falls.

The muscle connections from the lumbar spine to the upper thigh bone cause an increased forward pelvic tilt when the foot and leg rotate inwardly, which causes the body weight to shift forward greatly. It is this forward pelvic tilt that produces an increase in the lumbar curve of the spine. Furthermore, the upper thoracic vertebrae are also forced to increase its curve concurrently to compensate for changes in the low lumbar. The forward shift causes increase pressure on the forefoot, and more specifically, on an area where the metatarsal bones are located. These changes in the overall musculoskeletal system cause imbalance and wear on the joints, which can result in pressure on nerves causing pain.

Current insoles that are available lack a means of correcting musculoskeletal imbalances cheaply because such insoles require expensive molding techniques. Transferable insoles also lack a means of stabilizing the ankle and depend greatly on the shoe alone to give inadequate support the ankle requires. Moreover, insoles that do provide support under the plantar fascia tendons are generally fixated in an article of footwear and are not easily transferable.

Thus, there is a need for an orthotic insole usable in an article for footwear that corrects musculoskeletal imbalances beginning with the feet and continuing upward to the cervical vertebrae. A means of providing support to the ankle joint by such an othotic insole with a more secure fitting to the foot and shoe is also needed. Furthermore, there is a need for such an orthotic insole that absorbs shock while being easily inserted and transferable into various articles for footwear and adjustable for size to meet the preference of the user.

BRIEF SUMMARY OF THE INVENTION

The above-identified needs are addressed by the present orthotic insole. One feature of the present invention is an expandable rail section that is moveable from a receiving position to a grabbed position when the foot is placed in an article of footwear. In the preferred embodiment, the movement of the expandable rail section from the receiving position to the grabbed position is set in motion by a stabilization protrusion located on an under surface of a support base support base. An optional aspect of the present invention is an elevated region on the support base under a plantar fascia tendon region of the foot that corresponds to the anatomical structure of that foot. This optional aspect is designed to help correct musculoskeletal imbalances found in the body that begin at the foundation in the feet. In a preferred form, a shock absorbent piece is provided to reduce a shock force created when the heal of the foot produces an impact with a ground surface, also known as a heel strike. Another optional aspect of the present invention is a removable extension of the support base such that the support base is shortenable at a front end section.

More specifically, an orthotic insole usable in an article for footwear is provided that includes a support base for receiving a receivable member. An expandable rail section moveable between a receiving position and a grabbed position is associated with the support base along an outer perimeter of the support base. Furthermore, a means of moving the expandable rail section from the receiving position to the grabbed position when the receivable member is received on a top surface of the support base is also provided.

In an additional embodiment, an orthotic insole usable in an article for footwear includes a support base for receiving a receivable member and an expandable rail section moveable between a receiving position and a grabbed position when the receivable member is placed on the support base. The expandable rail section extends around an outer perimeter of the support base from a back part of the foot to a forward point located posterior to a metatarsal head area of the foot. A means of stabilizing the ankle of the foot is provided when the expandable rail section resides in the grabbed position when the foot is placed on a top surface of the support base.

In an additional embodiment, an orthotic insole usable in an article for footwear includes a shotenable support base for receiving a receivable member and an expandable rail section moveable between a receiving position and a grabbed position. The expandable rail section is positioned along an outer perimeter of the support base. A stabilization protrusion located on a bottom surface of the support base is also provided. The stabilization protrusion extends along an outer perimeter of the support base from a back part of the foot to a forward point located posterior to a metatarsal head area of the foot.

DETAILED DESCRIPTION OF THE INVENTION

Figure 1:
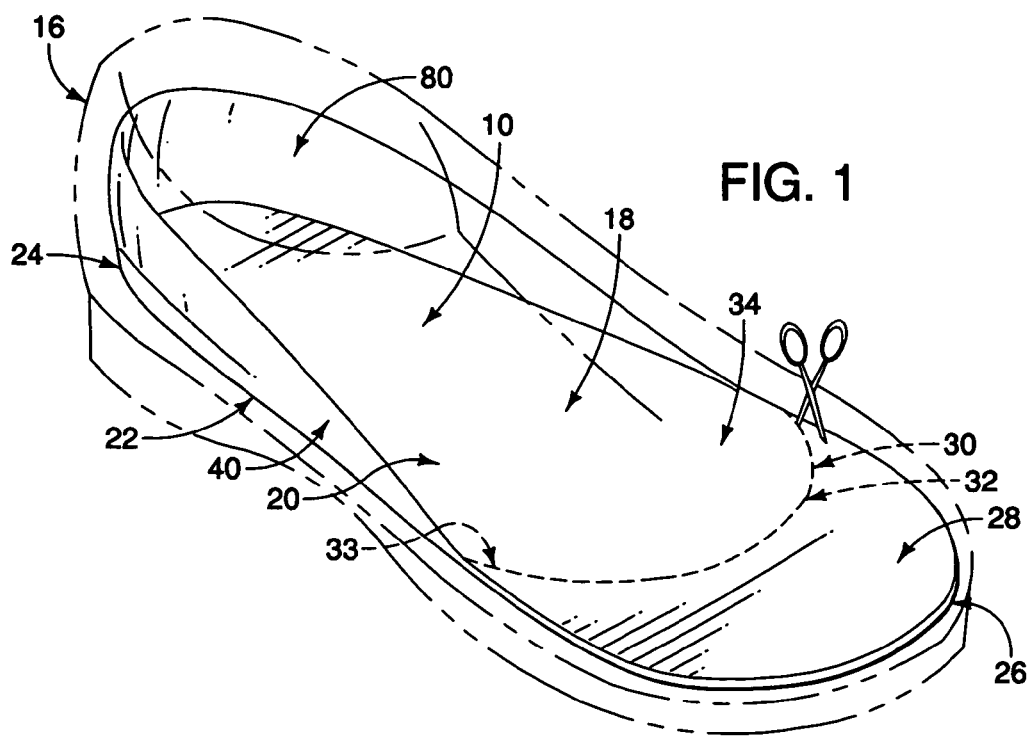
FIG. 1 is a side elevational view of an orthotic insole residing in an article of footwear.

Referring now to FIGS. 1, 3, 5 and 6, an orthotic insole usable in an article of footwear is generally designated 10. The orthotic insole 10 is designed for receiving a receivable member 12. The receivable member 12 is preferably a foot 14; however, it is appreciated that other types of receivable members 12 may be used such as a prosthetic foot or other extensions of a leg that is fitable onto the orthotic insole 10. For the orthotic insole 10 to provide balance and support for a body (not shown), the orthotic insole 10 preferably shaped to assist the foot 14 into alignment with its lower leg (not shown) as described below.

The orthotic insole 10 is adapted to fit into an article of footwear 16 by making the orthotic insole 10 sized to be insertable into the article for footwear 16. The article of footwear 16 is preferred to be a closed shoe, such as an athletic or leisure shoe; however, boots, sandals and other articles of footwear are also useable. The orthotic insole 10 is produced to accommodate the various sizes of the foot 14 and is customizable according to the specific needs of the foot 14. In the preferred embodiment, the orthotic insole 10 is made of a flexible material such as a plastic so that the orthotic insole 10 is manipulable to fit into the article of footwear 16. It is also preferred that the flexible material be resilient and soft such that the orthotic insole 10 is durable under wear and stress that comes with continued use, yet comfortable so that additional stress is not added to the foot 14. Furthermore, the flexible material of the orthotic insole 10 is preferred to have pliant properties such that the flexible material retains its general form once used or frayed. In the most preferred embodiment, a urethane plastic provides the desired properties to function as an effective insole.

A support base 18 for receiving the receivable member 12 provides a foundation 20 of support for the foot 14. The support base 18 is preferably of sufficient length and width such that a sole surface 22 of the article of footwear 16 is generally covered. The support base 18 in the preferred embodiment is extended approximately from a rear end 24 of the sole surface 22 to a front end 26 of the sole surface 22. The thickness of the support base 18 is preferably of a minimal depth to allow the foot 14 to fit comfortably into the article of footwear 16 while providing padding and comfort to the foot 14.

Now referring to FIG. 1, the support base 18 is preferably shortenable at a front end section 28 of the orthotic insole 10. It is preferred that the flexible material of the orthotic insole 10 is sufficiently delicate such that the front end section 28 of the support base 18 is shortenable by cutting, tearing, or other means of separation. The support base 18 is optionally provided with a cutting grove 30 that offers an easier means of shortening the orthotic insole 10. The cutting grove 30 is preferably a perforated cutting line 32 that etches small fissures 33 into a top surface 34 of the support base 18. Although the small fissures 33 are etchable through the entire thickness of the support base 18, it is preferred that only a minor indentation be used such that the small fissures 33 only penetrate the top surface 34 of the support base 18. It is also appreciated that a continuous etched grove (not shown) or other like means are also contemplated as being useable for the cutting grove 30.

Now referring to FIGS. 1, 2, 4, 5, 6 and 7, the support base 18 in the preferred embodiment is further provided with a shock absorbent piece 36 positioned to reduce a shock force of a heel strike 38. The shock force of a heel strike 38 occurs when pressure is applied from the weight of the receivable member 12 on the orthotic insole 10 by standing, walking, running, jumping or other like activity. The shock absorbent piece 36 is preferably situated below the top surface 34 of the support base 18 at a rear end section 40 of the orthotic insole 10. The shock absorbent piece 36 preferably covers a stress area 42 beneath the foot 14 such that heels bones and arch tendons (not shown) are supported. When the shock absorbent piece 36 is customized for the foot 14, the stress area 42 generally extends laterally from a rear end 24 below the sole surface 22 to a forward point 44 posterior to metatarsal heads of the foot 14. Shock absorbent materials used as the shock absorbent piece 36 for insoles are well known in the art. Politec® is one particular insert that is used in the most preferred embodiment to absorb floor reaction forces or the shock force of a heel strike 38.

Figure 5:
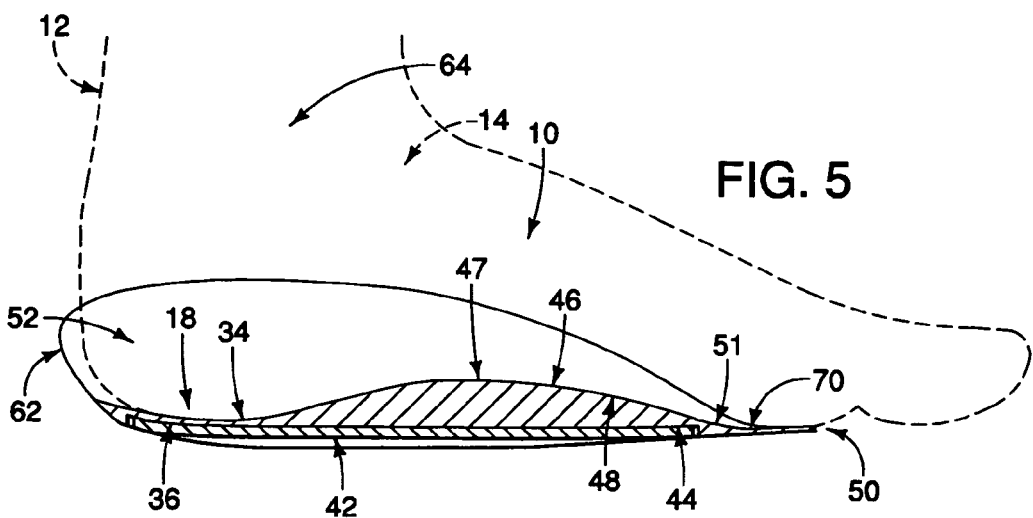
FIG. 5 is a side plan view of the orthotic insole and a foot residing the orthotic insole.

The stress area 42 is preferably further provided with an elevation 46 on the support base 18 under a plantar fascia tendon region 47 of the foot 14 (as shown in FIG. 5). The elevation 46 protrudes in an upward direction towards a bottom part 48 of the foot 14. By placing the elevation 46 directly beneath the plantar fascia tendon region 47, the slack that was present in the tendons is removed when standing on the support base 18. The removal of the slack in the tendons causes the bone structure to realign to its natural position. Thus the flattening out affect of the weakened tendons is artificially corrected by the elevation 46 by keeping the arch up and restoring the body's natural balance.

The height of the elevation 46 is dependent on the restoration requirement needed to achieve efficient biomechanical function of the foot 14. The elevation 46 is adjustable during manufacturing; however, a general minor elevation relative to a height of the front end section 50 of the orthotic insole 10 is all that is required when mass production for assembly were employed. Preferably, the height of the elevation 46 should not exceed the necessary requirement of that needed to return the arch to its natural position. The difference in height between the height of the front end section 50 and the elevation 46 is preferably bridged by a gradual slope 51 behind the forward point 44 posterior to metatarsal heads of the foot 14 (as shown in FIG. 5).

Now referring to FIGS. 3, 4, 5, 6 and 7, an expandable rail section 52 moveable between a receiving position 54 (FIG. 6) and a grabbed position 56 (FIG. 7) is associated with the support base 18 such that the expandable rail section 52 extends along an outer perimeter 58 of the support base 18. In the preferred embodiment, the expandable rail section 52 beings on a starting side 59 near the forward point 44 posterior to metatarsal heads of the foot 14 and extends around the rear end 24 of the sole surface 22 to finish at an opposing side 60 of the forward point 44. A rail height 62 of the expandable rail section 52 is preferably a function of the foot 14 such that effective support for an ankle 64 of the foot 14 is provided. To provide effective support for the ankle 64, the rail height 62 extends above an outermost point 66 of a concave curvature 68 of the foot 14. The rail height 62 is preferably shortened gradiently to a conversion point 70 where the rail height 62 is approximately equivalent to the height of the top surface 34. The conversion point 70 is located at or near the forward point 44 posterior to metatarsal heads of the foot 14.

The expandable rail section 52 is positioned to a receiving point 72 such that the expandable rail section 52 creates a gap 73 for the foot 14 while in the receiving position 54. The receiving point 72 resides preferably at a sufficiently wide point in an outward direction from the center of the support base 18 such that the receivable member 12 is receivable without collapsing the expandable rail section 52. The expandable rail section 52 extends outwardly beyond the foundation 20 to encompass the lower part of the foot 14. In the preferred embodiment, the receiving position 54 is the natural position of the orthotic insole 10 when no pressure or external stresses are applied to the orthotic insole 10.

Figure 2:
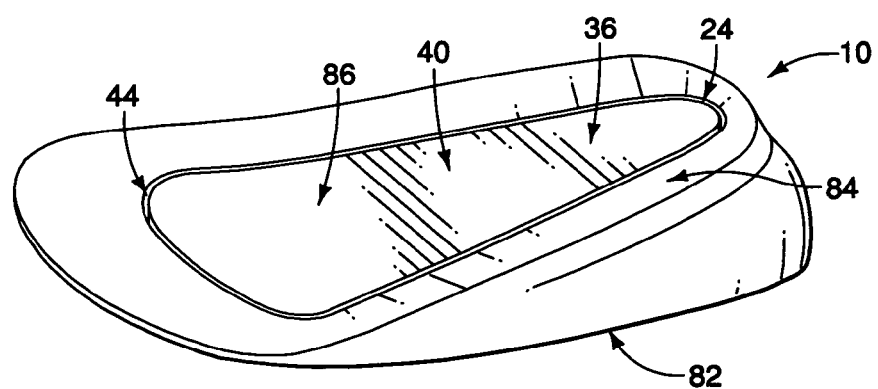
FIG. 2 is a bottom view of the orthotic insole as seen from a side perspective.
Figure 3:
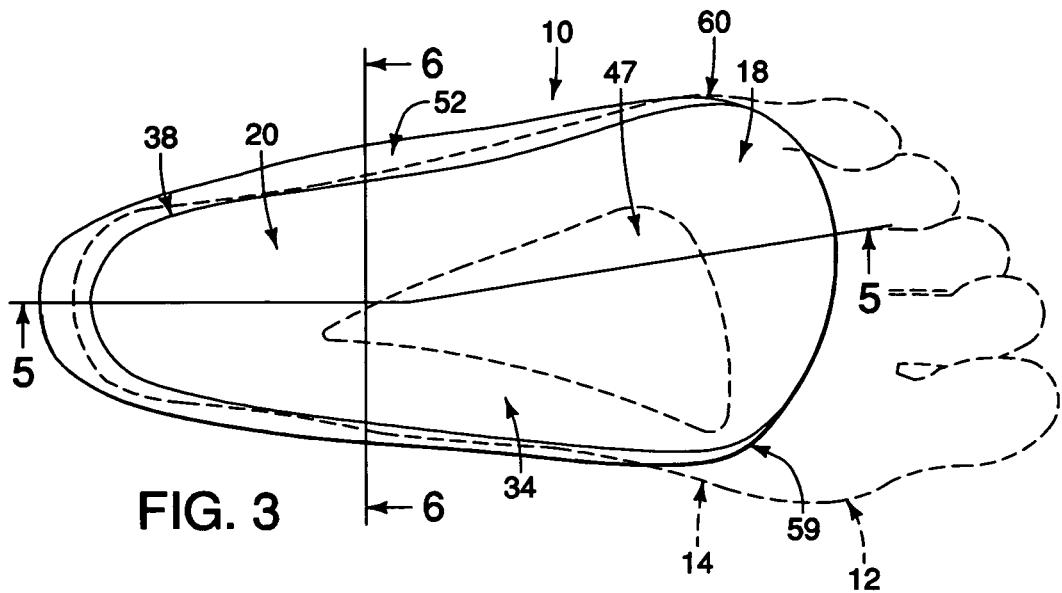
FIG. 3 is a top plan view of the orthotic insole and a foot residing in the orthotic insole.
Figure 4:
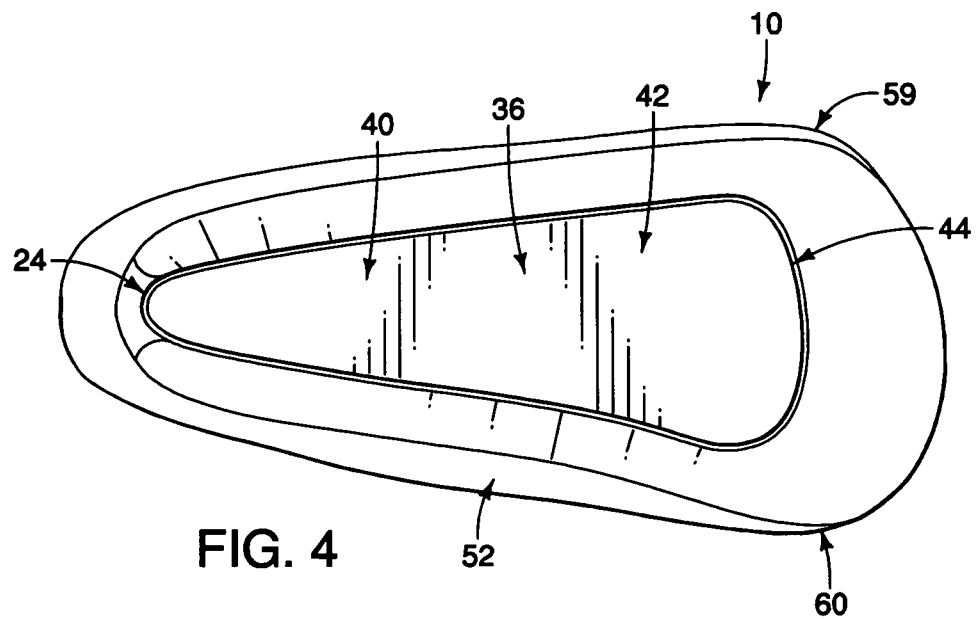
FIG. 4 is a bottom plan view of the orthotic insole.
Figure 6:
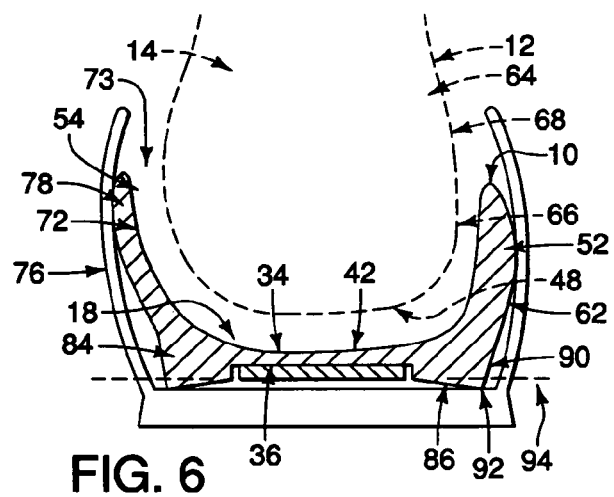
FIG. 6 is a rear perspective of the orthotic insole residing in a receiving position while placed in an article of footwear.

Now referring to FIGS. 1, 2 and 6, it is further preferred that the expandable rail section 52 is resideable in the receiving position 54 when placed in the article of footwear 16. The expandable rail section 52 is preferably kept approximate to or touching a shoe side wall 76 at a high end 78 of the expandable rail section 52 when placed inside the article of footwear 16 in the receiving position 54. Sufficient space is provided at a footwear opening 80 and between the gap 73 created by a top perimeter 82 of the high end 78 of the expandable rail section 52 to allow the receivable member 12 to fit in the article of footwear 16 unobstructed. The purpose of the resideable condition is to allow receivable member 12 to use the orthotic insole 10 while in the article of footwear 16. The same general receiving principles apply to the orthotic insole 10 either inside or outside the article of footwear 16. However, foot and ankle support are provided by the orthotic insole 10 while the receivable member 12 is in motion when used within the article of footwear 16, where only motionless foot and ankle support are provided when the orthotic insole 10 is used outside the article of footwear 16.

Figure 7:
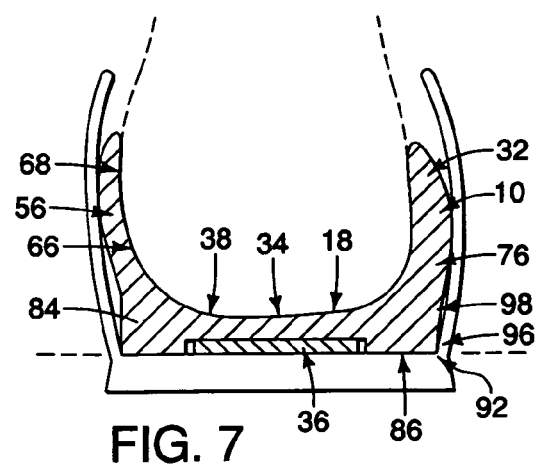
FIG. 7 is a rear perspective of the orthotic insole residing in a grabbed position while placed in an article of footwear.

Now referring to FIGS. 2, 6, and 7, when the receivable member 12 is placed on the top surface 34 of the support base 18, the expandable rail section 52 collapses to the grabbed position 56. The expandable rail section 52 is then positioned to securely form to the foot 14 or receivable member 12 while in the grabbed position 56 such that rolling of the ankle is limited, thus providing stability for the ankle joint.

A means of moving the expandable rail section 52 from the receiving position 54 to the grabbed position 56 when the receivable member is received on the top surface 34 of the support base 18 is preferably provided by a stabilization protrusion 84. The stabilization protrusion 84 is located on a bottom surface 86 of the support base 18. The stabilization protrusion 84 extends along the outer perimeter 58 of the support base 18 from a back part of the foot to a forward point 44 located posterior to a metatarsal head area of the foot. While in the receiving position 54, an outer edge 90 of the stabilization protrusion 84 is bowed in a slightly inward direction creating a concave curvature of the expandable rail section 52. A tip 92 of the stabilization protrusion 84 is preferably stretches below a plane 94 of the bottom surface 86 of the support base 18 when the expandable rail section 52 resides in the receiving position 54.

Placing the tip 92 below the plane 94 of the bottom surface 86 of the support base 18 allows a ground force to press up against the tip 92 as the receivable member 12 creates a downward static force into the sole surface 22 at or approximate to the center line 74 from the rear perspective. The tip 92 of the stabilization protrusion 84 is then forced to an upward position 96 approximately even with the plane 94 of the bottom surface 86 of the support base 18, compelling the expandable rail section 52 to the grabbed position 56. The outer edge 90 of said stabilization protrusion 85 is generally aligned in a linear manner with a lower part 98 of the expandable rail section 52 (as shown in FIG. 7), while the expandable rail section 52 retains the concave curvature 68.

A means of stabilizing the ankle of the foot 14 when the expandable rail section 52 resides in the grabbed position 56 is therefore provided when the foot 14 is placed on the top surface 34 of the support base 18. The means of stabilizing the ankle of the foot 14 is created when the expandable rail section 52 resides in the grabbed position 56 and the tip 92 of the stabilization protrusion 84 located on the bottom surface 86 flattens to an approximately even level with the plane 94 of the bottom surface 86 of the support base 18. While in the grabbed position 56, the stabilization protrusion 84 is bowed in a slightly outward direction from the position of the stabilization protrusion 84 found in the receiving position 54. In the receiving position 54, the stabilization protrusion 84 is found in a slightly bowed inward direction. The outward stretch of the stabilization protrusion 84 causes the support base 18 to extend planarly and grip a wider surface of the sole surface 22. Therefore, the support base 18 extends in a slightly outward direction when in the grabbed position 56 to offer lateral support to the foot 14 and the expandable rail section 52 prevents the foot 14 and ankle from rolling. Furthermore, by providing the support base with the elevation 46 under a plantar fascia tendon region of the foot 14, additional stabilization is also supplied to the foot 14 and the ankle of the foot 64.

While a particular embodiment of the present orthotic insole has been described herein, it will be appreciated by those skilled in the art that changes and modifications may be made thereto without departing from the invention in its broader aspects and as set forth in the following claims.

The invention claimed is:

1. An orthotic insole usable in an article for footwear for assisting in aligning a foot with its lower leg to provide balance and support, the orthotic insole comprising:
   a support base for receiving a receivable member;
   an expandable rail section moveable between a receiving position and a grabbed position, said expandable rail section is positioned along an outer perimeter of said support base; and
   a continuous stabilization protrusion located on a bottom surface of said support base for moving said expandable rail section from said receiving position to said grabbed position when said receivable member is received on a top surface of said support base, wherein said stabilization protrusion is bowed in an outward direction when in said grabbed position.

2. The orthotic insole of claim 1, wherein said orthotic insole is sized to be insertable into the article for footwear.

3. The orthotic insole of claim 1, wherein said support base is provided with a cutting grove at a front end section that extends the width of the orthotic insole.

4. The orthotic insole of claim 1, wherein said support base is further provided with a shock absorbent piece positioned to reduce a shock force of a heel strike.

5. The orthotic insole of claim 4, wherein said shock absorbent piece is situated below said top surface of said support base at a rear end section.

6. The orthotic insole of claim 1, wherein said support base is further provided with an elevation on said support base under a plantar fascia tendon region of the foot.

7. The orthotic insole of claim 1, wherein said expandable rail section extends around said outer perimeter of said support base from a rear end of said sole surface to a forward point located posterior to a metatarsal head area of the foot.

8. The orthotic insole of claim 7, wherein said expandable rail section is positioned to a receiving point such that said expandable rail section is receivable for the foot while in said receiving position.

9. The orthotic insole of claim 8, wherein said expandable rail section is resideable in said receiving position when placed in the article of footwear.

10. The orthotic insole of claim 7, wherein said expandable rail section is positioned to securely form to the foot while in said grabbed position.

11. The orthotic insole of claim 1, wherein said continuous stabilization protrusion extends along an outer perimeter of said support base from a back part of the foot to a forward point located posterior to a metatarsal head area of the foot.

12. The orthotic insole of claim 1, wherein an outer edge of said continuous stabilization protrusion is aligned in a linear manner with a lower part of said expandable rail section and a tip of said continuous stabilization protrusion is approximately even with a plane of said, bottom surface of said support base when said expandable rail section resides in said grabbed position.

13. The orthotic insole of claim 12, wherein said support base extends in an outward direction when in said grabbed position and grips a wider surface of a sole surface with said continuous stabilization protusion.

14. An orthotic insole usable in an article for footwear for assisting in aligning a foot with its lower leg to provide balance and support, the orthotic insole comprising:
  a support base for receiving a receivable member;
  an expandable rail section moveable between a receiving position and a grabbed position when a receivable member is placed on said support base, wherein said expandable rail section extends around an outer perimeter of said support base from behind a base section of the heel of the foot to a forward point located posterior to a metatarsal head area of the foot; and
  a continuous stabilization protrusion located on a bottom surface of said support base for stabilizing an ankle of the foot when said expandable rail section resides in said grabbed position when the foot is placed on a top surface of said support base.

15. The orthotic insole of claim 14, wherein the ankle of the foot is stabilized when said expandable rail section resides in said grabbed position by said stabilization protrusion located on a bottom surface of said support base bowed in an outward direction and a tip of said stabilization protrusion is approximately even with a plane of said bottom surface of said support base.

16. The orthotic insole of claim 14, wherein said support base is further provided with an elevation on said support base under a plantar fascia tendon region of the foot.

17. The orthotic insole of claim 14, wherein said support base is provided with a cutting grove at a front end section that extends the width of the orthotic insole.

18. An orthotic insole usable in an article for footwear for assisting in aligning a foot with its lower leg to provide balance and support, the orthotic insole comprising:
  a support base for receiving a receivable member, said support base is provided with a cutting grove at a front end section;
  an expandable rail section moveable between a receiving position and a grabbed position, said expandable rail section is positioned along an outer perimeter of said support base;
  an elevation found on said support base located beneath a plantar facia tendon region of the foot; and
  a continuous stabilization protrusion located on a bottom surface of said support base, said stabilization protrusion extends along an outer perimeter of said support base from a back part of the foot to a forward point located posterior to a metatarsal head area of the foot.

* * * * *